(12) United States Patent
Hunt et al.

(10) Patent No.: US 6,476,293 B1
(45) Date of Patent: Nov. 5, 2002

(54) USE OF BACTERIAL ACETATE KINASE AND THEIR GENES FOR PROTECTION OF PLANTS AGAINST DIFFERENT PATHOGENS

(75) Inventors: Arthur G. Hunt; Glenn B. Collins; Christopher Lawrence; Qingshun Li, all of Lexington, KY (US); Santanu Dasgupta, Bangalore (IN)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/410,023

(22) Filed: Oct. 1, 1999

(51) Int. Cl.$^7$ .......................... A01H 3/00; C07H 21/04; C07K 14/195; C12N 5/14; C12N 9/00
(52) U.S. Cl. ..................... 800/279; 800/301; 435/69.1; 435/70.1; 435/194; 435/414; 435/183; 435/419; 435/418; 435/320.1; 536/23.2; 536/23.7; 536/24.1
(58) Field of Search ................................. 800/279, 301; 435/69.1, 70.1, 194, 414, 183, 419, 418, 320.1; 536/23.2, 23.7, 24.1

(56) References Cited

U.S. PATENT DOCUMENTS

| | | | |
|---|---|---|---|
| 5,597,946 A | | 1/1997 | Jaynes et al. |
| 5,648,599 A | * | 7/1997 | Tanksley et al. |
| 5,859,351 A | | 1/1999 | Staskawicz et al. |

FOREIGN PATENT DOCUMENTS

| | | |
|---|---|---|
| AU | 715002 | 6/1996 |
| WO | WO 95/05731 | 3/1995 |
| WO | WO 96/17069 | 6/1996 |
| WO | 98/18939 | 5/1998 |
| WO | WO 99/02655 | 1/1999 |

OTHER PUBLICATIONS

Matsuyama et al. J. Bacteriol. Jan. 1989, p. 577–580 vol. 171, No. 1.*

Dasgupta, et al. Co–ordinated expression of multiple enzymes in different subcellular compartments in plants. The Plt. Jour. 16 (1), 107–116, 1998.*

Linthorst, et al, The Plant Cell, vol. 1, 285–291, 1989.*

Maiti et al., "Plants that expresss a potyvirus proteinase gene are resistant to virus infection," *Proc. Natl. Acad. Sci. USA* 90:6110–6114 (1993).

"Co–ordinated Expression of Multiple Enzymes in Different Subcellular Compartments in Plants", by Dasgupta et al., The Plant Journal, vol. 16, No. 1, pp. 107–116, 1998.

"Approaches and Progress in the Molecular Cloning of Plant Disease Resistance Genes", by Bennetzen et al., Genetic Engineering, vol. 14, pp. 99–124, 1992.

"Expression of Bacterial Genes in Plant Cells", by Fraley et al., Proc. Natl. Acad. Sci. USA, vol. 80, pp. 4803–4807, Aug. 1983.

"Design and Construction of a Versatile System for the Expression of Foreign Genes in Plants", by Schardl et al., 1987 Elsevier Science Publishers B.V., vol. 61, pp. 1–11, 1987.

"Protein Targeting and Integration Signal for the Chloroplastic Outer Envelop Membrane", by Li et al., The Plant Cell, vol. 8, pp. 2117–2125, Nov. 1996.

"Expression of the *Escherichia coli* fabA Gene Encoding β–hydroxydecanoyl Thioester Dehydrase and Transport to Choloplasts in Transgenic Tobacco", by Saito et al., Transgenic Research, vol. 4, pp. 60–69, 1995.

"The Synthesis and Possible Functions of Virus–Induced Proteins in Plants", by Bol et al., Microbiological Sciences, vol. 5, No. 2, pp. 47–52, Jan. 1988.

\* cited by examiner

Primary Examiner—Phuong T. Bui
(74) Attorney, Agent, or Firm—Clark & Elbing LLP

(57) ABSTRACT

An isolated gene fragment that encodes for acetate kinase, which confers disease resistance in plants is disclosed. The gene can be cloned into an expression vector to produce a recombinant DNA expression system suitable for insertion into cells to form a transgenic plant transformed with the gene fragment. A method for conferring disease resistance in plants that consists of growing plant host cells transformed with the expression system and expressing the gene conferring disease resistance to impart such resistance to host cells is also disclosed.

7 Claims, 5 Drawing Sheets

USE OF BACTERIAL ACETATE KINASE AND THEIR GENES FOR PROTECTION OF PLANTS AGAINST DIFFERENT PATHOGENS

TECHNICAL FIELD

The present invention generally relates to an isolated gene fragment that encodes for acetate kinase, which confers disease resistance in plants. The gene can be cloned into an expression vector to produce a recombinant DNA expression system suitable for insertion into cells to create a transgenic plant containing the gene fragment. The present invention also relates to a method for conferring disease resistance in plants that consists of growing plant host cells transformed with the expression system and expressing the gene to impart such resistance to host cells. More particularly, the present invention relates to the introduction of bacterial acetate kinase (ack) into plants to induce systemic acquired resistance; a chimeric gene construct containing the ack sequence; an expression vector containing the chimeric gene construct; a plant cell transformed with the chimeric gene construct; a plant tissue transformed with the chimeric gene construct; and a transgenic plant transformed with the chimeric gene construct.

BACKGROUND ART

Pathogen defense in plants is a varied and complicated process, involving a host of local and systemic events geared towards arresting growth of a pathogen. The cascade of events that lead to pathogen resistance is usually triggered by recognition of any of a range of pathogen-produced molecules (or elicitors (1–3)), and involves rapid local responses (such as ion fluxes and production of reactive oxygen species at the site of ingress (4–6)) and more prolonged local and systemic events (localized cell death, production of poorly understood translocated messengers, and induction of the expression of genes whose products act to limit the spread of pathogens (7,8). These recognition events are often mediated by specific pairs of molecules—pathogen-derived elicitors and cognate plant-encoded receptors (9–15). These receptors, when "activated" by their respective ligands, trigger a large number of subsequent events that are themselves mediated by a number of signaling pathways.

Interestingly, plants undergo similar responses when challenged by pathogenic organisms and by organisms that do not cause disease. Thus, in both instances, systemic induction of so-called defense genes occurs. However, in the case where resistance is to be manifest, a rapid response is apparent and can include localized cell death referred to as the hypersensitive response (HR), while a slower response occurs in cases where disease is the ultimate result. These observations serve to emphasize the fact that the timing of a response is an important factor in disease resistance in plants (16,17). Thus, while much is known about the signaling events involving early (local) and late (systemic) responses to pathogens, much remains to be learned regarding the multiplicity of signaling pathways and the integration of multiple pathways.

SUMMARY OF THE INVENTION

The present invention is the introduction of a gene encoding acetate kinase into plant cells and plants to increase their resistance to bacterial and fungal pathogens.

The invention provides novel chimeric gene constructs that contain an ack coding sequence.

The invention also provides transformed plant cells and transgenic plants transformed with novel chimeric gene constructs that contain the ack coding sequence.

The invention thus provides a method for the expression of the ack gene in the cytoplasm of plant cells and plants.

Additional advantages of the present invention will be set forth in the description and examples that follow, or may be learned from practicing the invention. These and other advantages may be realized and attained by means of the features, instrumentalities and/or combinations particularly described herein. It is also to be understood that the foregoing general description and the following detailed description are only exemplary and explanatory and are not to be viewed as limiting or restricting the invention as claimed.

The invention itself, together with further advantages, will best be understood by reference to the following detailed description, taken in conjunction with the accompanying drawings.

DETAILED DESCRIPTION OF THE INVENTION

All patents, patent applications and literatures that may be cited in this description are incorporated herein by reference in their entirety.

Figure 1:
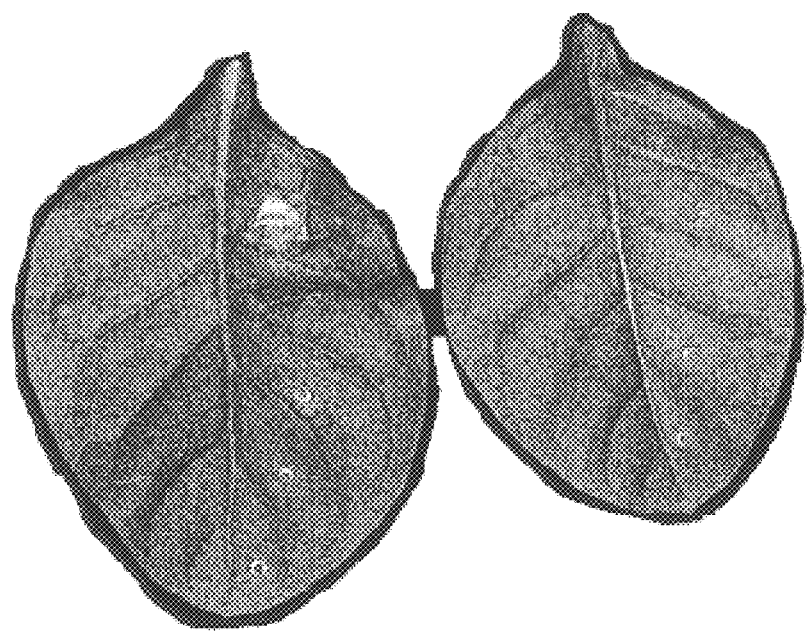
FIG. 1 shows resistance of AK tobacco plants to wildfire (a bacterial pathogen). (See legends to FIGS. 2 and 3 for methods.)

In the course of studies dealing with strategies for expressing multiple genes in plants (18), it was observed that tobacco plants that express the *E. coli* acetate kinase (ack) gene (in the cytoplasm) seemed to retain a healthy appearance in the greenhouse after other neighboring plants (not possessing this gene) had begun to show signs of disease and/or senescence. For this reason, a limited battery of pathogenicity tests was conducted. Specifically, ack-transformed tobacco were tested for their responses to *Pseudomonas syringe* pv. *tabaci* WF4, a bacterial pathogen of tobacco. The results of these tests were dramatic, in that plants with cytoplasmically localized acetate kinase (AK) were significantly resistant to this pathogen (FIG. 1). In contrast, untransformed plants as well as plants expressing a chloroplast-targeted form of AK were susceptible to infection by this pathogen.

Figure 2:
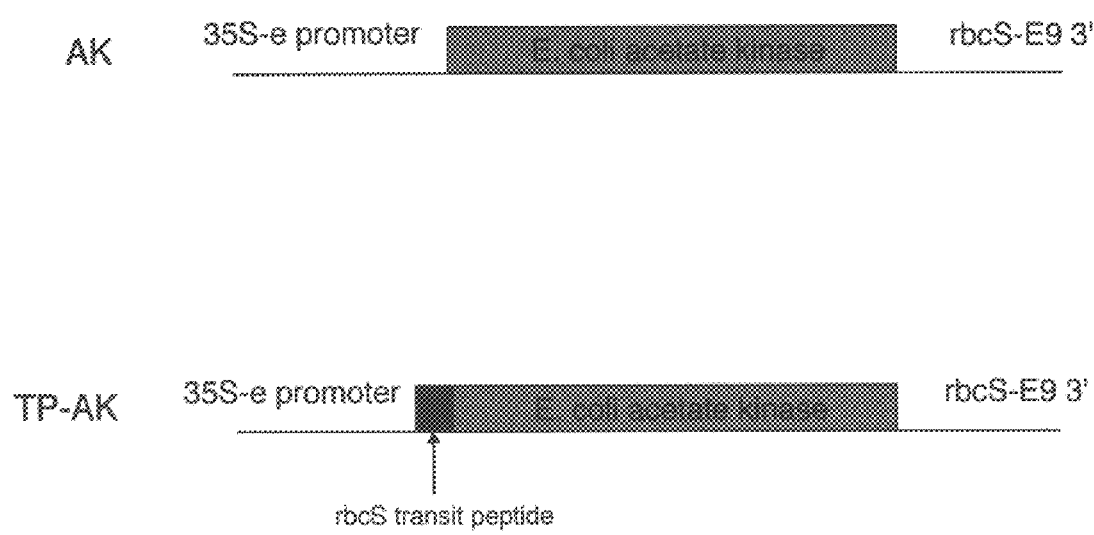
FIG. 2 shows assembly of the constructs used in plant transformation: cytoplasmic vs. chloroplast-localized AK, untransformed controls.

To explore this phenomenon in more detail, we elected to express the ack gene in Arabidopsis. For this, two constructs were used—one in which the AK would be localized to the cytoplasm (FIG. 2), and one in which the acetate kinase would reside in the chloroplast (termed here as TP-AK (FIG. 2)). The results of this process were a number of transgenic Arabidopsis lines that carried the AK and the TP-AK gene. Plants that expressed detectable quantities of the AK gene product were identified by immunoblot analysis (not shown)

and several of these selected for further study. The AK-containing Arabidopsis plants thrived and were fertile.

Figure 3A:
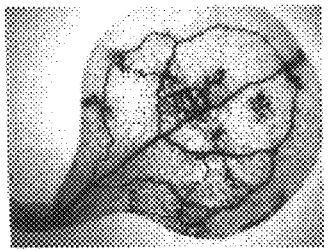
FIGS. 3A–3C show the results of *Peronospora parasitica* (a fungal pathogen) tests: (A) infected control; (B) spores on infected control; and (C) autofluorescence.
Figure 3B:
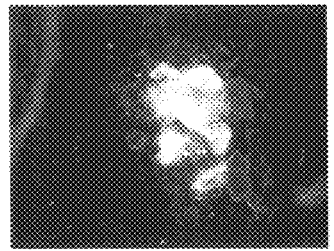
Figure 3C:
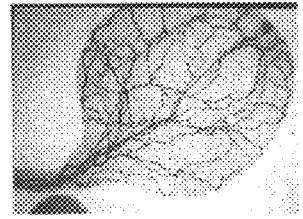

AK Arabidopsis plants proved to be highly resistant to an isolate of *Peronospora parasitica* capable of causing disease on the untransformed parent and on TP-AK-containing plants. On untransformed control plants and TP-AK plants, spores were able to germinate and grow throughout infected leaves, and eventually into other parts of the plant (FIG. 3A). In contrast, on AK plants, spores rarely germinated, and those that did grew only a minimal distance (FIG. 3B). In addition, spore germination and invasion on AK plants was accompanied by the appearance of localized autofluorescent material (FIG. 3C) indicative of a strong hypersensitive response. The combination of limited germination and growth resulted in a virtual lack of disease symptoms in inoculated plants (not shown). This resistance corroborates the results obtained with the tobacco lines, and suggests that AK expressing Arabidopsis can respond very rapidly to limit the growth and spread of the oomycete pathogen. In addition, the lack of resistance that was observed in TP-AK plants indicates that a specific subcellular location is required for the effects of the ack gene.

Figure 4:
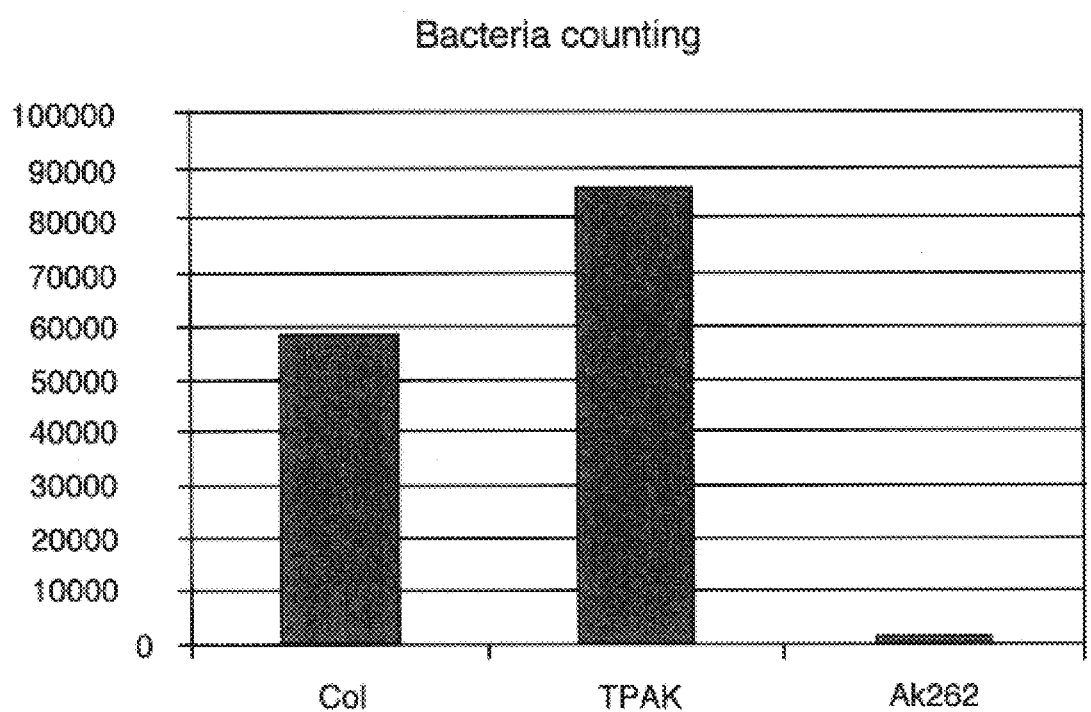
FIG. 4 shows resistance of AK plants to *Pseudomonas syringe* pv. maculicola ES 4326 (a bacterial pathogen).

Additional tests were conducted with a bacterial pathogen (*Pseudomonas syringae* pv *maculicola* ES 4326). As was observed with *P. parasitica*, AK-containing Arabidopsis were highly resistant to this pathogen. Specifically as seen in FIG. 4, a minimum of bacterial growth was seen on the AK plants, in contrast to the extensive growth observed on the untransformed and TP-AK plants.

Figure 5A:
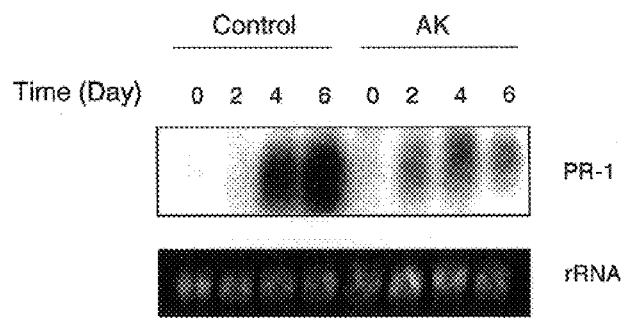
FIGS. 5A–5B show the level of PR gene expression in uninoculated AK plants untransformed control lines before inoculation (FIG. 5A) and after inoculation (FIG. 5B).
Figure 5B:
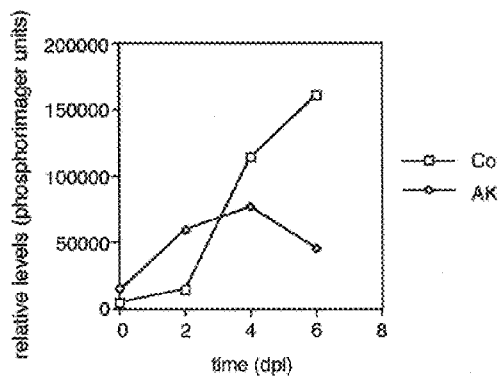

Disease resistance in transgenic plants is often associated with elevated and constitutive expression of a range of genes associated with systemic acquired resistance (19). Accordingly, the levels of expression of so-called PR genes (20) were determined in various of these lines. In uninoculated AK plants, a low but significant level of PR gene expression was observed (FIG. 5). In contrast, with untransformed control lines, no detectable PR gene expression was apparent in the absence of inoculation with pathogens (FIG. 5). After inoculation with *P. parasitica*, PR gene expression was dramatically induced in the AK plants (FIG. 5), beginning in two days and reaching the highest levels after 4 days. In contrast, for as much as 2 days, PR gene expression remained very low in control plants that had been inoculated with *P. parasitica* (FIG. 5). Interestingly, at later times after inoculation, PR gene expression in control plants rose to levels that exceeded those seen in AK plants, even though the control plants developed disease symptoms.

The presence of a low level of PR gene expression in uninoculated AK plants suggests that the expression of the ack gene in Arabidopsis induces constitutive systemic acquired resistance (SAR), perhaps analogous to that seen in several Arabidopsis mutants (19, 24–29). However, the very low PR gene expression in these plants, and the rapid increase in these levels upon challenge with pathogens, is distinctive. In addition, the deposition of autofluorescent material near the sites of germinating spores (FIG. 3C), along with the altered kinetics of response of PR gene expression and SA synthesis in the AK plants, suggests that the expression of the ack gene in Arabidopsis has in some way conditioned these plants for a rapid response to what is otherwise a virulent pathogen. In other systems, the difference between rapid response (and subsequent HR and resistance) and slow response (thereby permitting disease development) has been linked to the ability of the host plant to recognize specific pathogen-derived signals (elicitors (30)). One might hypothesize that the expression of the ack gene in Arabidopsis in some way mimics this recognition process, perhaps by elevating the expression of resident (unexpressed) R genes in Arabidopsis. However, other properties of the AK plants argue against this. For example, tomato plants that express the Pto gene in a constitutive manner are resistant to a range of pathogens not normally dependent upon Pto-mediated elicitor recognition, but these plants also possess micro-HR lesions and high constitute SA and PR gene expression (31). Likewise, plants that express various R-gene-independent harpin genes (such as hrmA) are also resistant to a broad range of pathogens, and possess elevated SA and PR gene expression (32,33). In contrast, uninoculated AK plants lack detectable microlesions and have normally modest SA (not shown) and PR gene expression levels.

In bacteria, the expected metabolic product of the expression of the ack gene (acetyl phosphate) can gratuitously phosphorylate two-component receiver modules in bacteria, and such modifications may play important roles in the regulation of responses to osmotic changes or phosphate status (34–36). Moreover, phosphorylated acetate kinase can itself transfer this phosphate to enzyme I of the phosphoenolpyruvate:glucose phosphotransferase system (PTS; 37). Given these precedents, our results suggest an involvement of a two-component-like signaling pathway in the development of the hypersensitive response in plants. The effects of the ack gene in Arabidopsis would thus be explained by analogy with prior studies in bacteria—one (or more) of the components of this hypothetical pathway would be gratuitously phosphorylated (by phosphorylated acetate kinase, as is seen with enzyme I of the PTS (37), or by acetyl phosphate (34–36), thereby altering the activity status of the rest of the pathway, resulting in an ability to respond rapidly and effectively to otherwise pathogenic microorganisms. This eventuality would insert an additional layer of complexity in the defense signaling network in plants. In particular, it would imply a separate signaling pathway that functions to facilitate rapid local and systemic defense responses.

At this time, however, an indirect effect is equally likely. As is to be expected, defense responses in plant are integrated with many other signaling pathways; these include pathways that mediate the actions of ethylene, cytokinin, jasmonate. Interestingly, two-component-like factors have been implicated in ethylene (38) and cytokinin signaling (39–41). The general appearance of the AK plants is relatively normal and does not suggest a dramatic and general effect on ethylene- or cytokinin- related responses. However, given the multiplicity of histidine-kinase-related ethylene receptors in Arabidopsis (38,42), and a similar multiplicity of cytokinin-inducible response regulators (39–41), it remains possible that selective modification of a small subset of these can lead to the pre-conditioning for rapid defense responses that is seen in AK plants. This model is intriguing in that it suggests that rapid defense responses might be affected, or conditioned, by factors in addition to pathogen recognition.

To summarize, the present invention demonstrates that the expression of the *E. coli* acetate kinase gene in Arabidopsis can pre-condition Arabidopsis for rapid and effective defense responses against otherwise pathogenic microorganisms. This invention indicates that rapidity of response can be manipulated in novel ways, without grossly changing the health of the plant. It also shows that rapidity of response is a viable target for modification as it relates to improving the disease defense characteristics of crop plants. Finally, the invention suggests that two-component signaling systems may be directly or indirectly involved in determining the rapidity with which Arabidopsis responds to challenge by pathogens.

Methods

The AK coding sequence was isolated by PCR from *E. coli* genomic DNA as described by Dasgupta et al. (18). This gene was subcloned into pKYLX71:35S$^2$ (21) as an XhoI-SacI fragment. The TP-AK gene was assembled basically as described by Dasgupta et al. (18) and also subcloned into pKYLX71:35S$^2$ as an XhoI-SacI fragment. The recombinant plasmids were mobilized into *Agrobacterium tumefaciens* C58C1:pGV3850 (22) and transconjugants used to transform Arabidopsis (ecotype Columbia) by vacuum infiltration. Transformed plants were identified by selection on agarose media containing kanamycin (50 µg/ml). Expression of the transgene was assessed by immunoblot analysis. 500 mg of leaves from transgenic plants were homogenized in 1 ml of extraction buffer (0.0625 M Tris-HCl, pH 6.8/10% glycerol/2% SDS/10% 2-mercaptoethanol), boiled for 10 min and centrifuged at 12,000 g for 10 min. 50 µg of total protein were separated on 12.5% polyacrylamide gel containing SDS, transferred to nitrocellulose membrane, and probed with the appropriate antisera (23). Antigen-antibody complexes were visualized using HRP conjugated anti-rabbit IgG using a chemiluminesence kit (NEN Life Sciences).

Resistance to fungal infections was assessed using a compatible isolate *Peronospora parasitica* noco2. For inoculations, spores were collected from sporulating susceptible arabidopsis plants, washed with deionized water, and suspended in water to a concentration of 50,000 spores/ml. Plants were sprayed with this suspension and kept in a high humidity growth chamber. Plants were examined visually and microscopically as shown. Autofluorescence was visualized using a fluorescent microscope under UV light.

Pseudomonas syringe pv. maculicola ES 4326 was grown in liquid Luria Bertani (LB) medium with 100 mg/1 streptomycin at 28° C. overnight, collected by centrifugation, and resuspended in 10 mM MgCl$_2$, and adjusted to cell density of $OD_{600}$=1.0. The $OD_{600}$=1.0 bacterial suspension was diluted 250 times, then 10 µl were infiltrated to the leaves. After 5 days, leaves were collected, washed to remove incipient bacteria, and the bacteria counted by plating serial dilutions on media.

PR gene expression was measured by northern blot analysis (23). Total RNA was isolated from the leaves of 2–3 week old plants, or the plants spread by *P. parasitica*, using the RNAqueous total RNA isolation Kit (Ambion Inc., Austin, Tex.). Equal amounts of total RNA (10 µg) were resolved on a 1.2% (w/v) agarose/formaldehyde gel containing 1×3-(N-morpholino-)propanesulfonic acid (MOPS) buffer, and transferred to a Nytran membrane (Schleicher & Schuell, Keene, NH). Membranes were hybridized with a $^{32}$P-labeled DNA probe generated using the Prime-it II Random Primer Labeling kit (Stratagene, La Jolla, Calif.), washed using standard protocols (23), and visualized by autoradiography on X-ray film.

References

1. Dangl, J. L., Dietrich, R. A., and Richberg, M. H. (1996). Plant Cell 8, 1793–1807.
2. Baker, B., Zambryski, P., Staskawicz, B., and Dinesh-Kumar, S. P. (1997). Science 276, 726–33
3. Hammond-Kosack, K. E., and Jones, J. D. (1996). Resistance gene-dependent plant defense responses. Plant Cell 8, 1773–91.
4. Blumwald, E., S., A. G., and Lam, B. C.-H. (1998). Trends in Plant Science 9, 342–346.
5. Xing, T., Higgins, V. J., and Blumwald, E. (1996). Plant Cell 8, 249–259.
6. Xing, T., Higgins, V. J., and E., B. (1997). Plant Cell 9, 249–259.
7. Ryals, J. A., Neuenschwander, U. H., Willits, M. G., Molina, A., Steiner, H.-Y., and Hunt, M. (1996). Plant Cell 8, 1809–1819
8. Sticher, L., Mauch-Mani, B., and Metrauz, J. P. (1997). Ann. Rev. Phytopathol. 35, 235–270.
9. Bent, A. F., Kunkel, B. N., Dahlbeck, D., Brown, K. L., Schmidt, R., Giraudat, J., Leung, J., and Staskawicz, B. J. (1994). Science 265, 1856–60.
10. Botella, M. A., Parker, J. E., Frost, L. N., Bittner-Eddy, P. D., Beynon, J. L., Daniels, M. J., Holub, E. B., and Jones, J. D. (1998). Plant Cell 10, 1847–60.
11. Grant, M. R., Godiard, L., Straube, E., Ashfield, T., Lewald, J., Sattler, A., Innes, R. W., and Dangl, J. L. (1995). Science 269, 843–6.
12. Greenberg, J. T., Guo, A., Klessig, D. F., and Ausubel, F. M. (1994). Cell 77, 551–63.
13. Martin, G. B., Brommonschenkel, S., Chunwongse, J., Frary, A., Ganal, M. W., Spivey, R., Wu, T., Earle, E. D., and Tanksley, S. D. (1993). Science 262.
14. Salmeron, J. M., Oldroyd, G. E., Rommens, C. M., Scofield, S. R., Kim, H. S., Lavelle, D. T., Dahlbeck, D., and Staskawicz, B. J. (1996). Cell 86, 123–33.
15. Song, W. Y., Wang, G. L., Chen, L. L., Kim, H. S., Pi, L. Y., Holsten, T., Gardner, J., Wang, B., Zhai, W. X., Zhu, L. H., and et al. (1995). Science 270, 1804–6.
16. Lebrun-Garcia, A., Ouaked, F., Chiltz, A., and Pugin, A. (1998). Plant J 15, 773–81.
17. Romeis, T., Piedras, P., Zhang, S., Klessig, D. F., Hirt, H., and Jones, J. D. (1999). Plant Cell 11, 273–87.
18. Dasgupta, S., Collins, G. B., and Hunt, A. G. (1998) .Plant J. 26, 107–116.
19. Cao, H., Li, X., and Dong, X. (1998). Proc Natl Acad Sci U S A 95, 6531–6.
20. Rogers, EE. and Ausubel, F. M. (1997).Plant Cell 9, 305–16.
21. Maiti, I. B., Murphy, J. F., Shaw, J. G., and Hunt, A. G. (1993). Proc. Natl. Acad. Sci. USA 90, 6110–6114.
22. Schardl, J., Byrd, A. D., Benzion, G., Altschuler, M., Hildebrand, D. F., and Hunt, A. G. (1987). Gene 61, 1–11.
23. Sambrook J, Fritsch EF, Maniatis T (1989) Molecular Cloning: A Laboratory Manual, Cold Spring Harbor, Cold Spring Harbor, N.Y.
24. Bowling, S. A., Guo, A., Cao, H., Gordon, A. S., Klessig, D. F., and Dong, X. (1994). Plant Cell 6, 1845–57.
25. Cao, H., Bowling, S. A., S., G. A., and Dong, X. (1994). Plant Cell 6, 1583–1592.
26. Dietrich, R. A., Delaney, T. P., Uknes, S. J., Ward, E. R., Ryals, J. A., and Dangl, J. L. (1994). Cell 77, 565–77.
27. Parker, J. E., Holub, E. B., Frost, L. N., Falk, A., Gunn, N. D., and Daniels, M. J. (1996). Plant Cell 8, 2033–46.
28. Shah, J., Kachroo, P., and Klessig, D. F. (1999). Plant Cell 11, 191–206
29. Weymann, K., Hunt, M., Uknes, S., U., N., Lawton, K., Steiner, H. Y., and Ryals, J. (1995). Plant Cell 7, 2013–2022.
30. Kuc, J. and Rush, J. S. (1985) Arch. Biochem. Biophys. 236, 455–472.
31. X. Tang, M. Xie, Y. J. Kim, J. Zhou, D. F. Kessig, and G. B. Martin. (1999). Plant Cell 11, 15–29.
32. Shen, S., Li, Q., He, S.-Y., Barker, K. R., Li, D., and Hunt, A. G., manuscript submitted.
33. Oldroyd, G. E. D. and Staskawicz, B. J. (1998) Proc. Nat. Acad. Sci. USA 95, 10300–10305.
34. McCleary, W. R. and Stock, J. B. (1994). J Biol Chem 269, 31567–72.

35. Kim, S. K., Wilmes-Riesenberg, M. R., and Wanner. B. L. (1996) Mol. Microbiol. 22, 135–147.
36. Bouche, S., Klauck, E., Fischer, D., Lucassen, M., Jung, K., and Hengge-Aronis, R. (1998). Mol Microbiol. 27, 787–95.
37. Fox, D. K., Meadow, N. D., and Roseman, S. (1986). J Biol Chem 261, 13498–503.
38. Gamble, R. L., Coonfield, M., L., and Schaller, E. G. (1998) Proc. Nat. Acad. Sci. USA 95, 7825–7829.
39. Kakimoto, T. (1996) Science 274, 982–985.
40. Sakakibara, H., Suzuki, M., Takei, K., Deji, A., Taniguchi, M., and Sugiyama, T. (1998). Plant J. 14, 337–344.
41. Taniguchi, M., Kiba, T., Sakakibara, H., Ueguchi, C., Mizuno, T., and Sugiyama, T. (1998). FEBS Lett. 429, 259–262 (1998).
42. Hua, J., Sakai, H., Nourizadeh, S., Chen, Q. G., Bleecker, A. B., Ecker, J. R., and Meyerowitz, E. M. (1998) Plant Cell 10, 1321–32.

What is claimed is:

1. A method of conferring to a plant resistance to a fungal or bacterial pathogen, said method comprising regenerating a plant from plant cells expressing a chimeric nucleic acid molecule comprising in the 5' to 3' direction: (i) a promoter functional in a plant nucleus operably linked to (ii) a nucleic acid molecule or fragment thereof encoding a bacterial polypeptide having acetate kinase activity operably linked to (iii) a non-translated region of a nucleic acid molecule said region encoding an mRNA polyadenylation site, wherein expression of said chimeiic nucleic acid molecule in said plant confers resistance to a fungal or bacterial pathogen.

2. The method of claim 1, wherein said bacterial polypeptide is an *E. coli* acetate kinase polypeptide.

3. The method of claim 1, wherein said plant is resistant to a fungal pathogen.

4. The method of claim 3, wherein said fungal pathogen is Peronospora.

5. The method of claim 1, wherein said plant is resistant to a bacterial pathogen.

6. The method of claim 5, wherein said bacterial pathogen is Pseudomonas.

7. The mcthod of claim 1, wherein said plant is a tobacco plant.

* * * * *

UNITED STATES PATENT AND TRADEMARK OFFICE
CERTIFICATE OF CORRECTION

PATENT NO. : 6,476,293 B1
DATED : November 5, 2002
INVENTOR(S) : Arthur G. Hunt et al.

It is certified that error appears in the above-identified patent and that said Letters Patent is hereby corrected as shown below:

Column 5,
Line 33, replace "Pseudomonas syringe" with -- *Pseudomonas syringe* --.

Column 6,
Line 60, replace "Kessig" with -- Klessig --.

Column 8,
Line 7, replace "chimeiic" with -- chimeric --.
Line 15, replace "Peronospora" with -- *Peronospora* --.
Line 19, replace "Pseudomonas" with -- *Pseudomonas* --.

Signed and Sealed this

Twenty-second Day of March, 2005

JON W. DUDAS
*Director of the United States Patent and Trademark Office*